United States Patent [19]

Lerner

[11] Patent Number: 4,524,760

[45] Date of Patent: Jun. 25, 1985

[54] SEXUAL AID

[76] Inventor: Elaine Lerner, 6 Duggan St., Stoughton, Mass. 02072

[21] Appl. No.: 499,507

[22] Filed: May 31, 1983

[51] Int. Cl.[3] .................. A61B 19/00

[52] U.S. Cl. .................. 128/1 R; 128/98

[58] Field of Search .......... 2/44; 128/1 R, 132-134, 128/138, 95-99, 155, 524, 531

[56] References Cited

U.S. PATENT DOCUMENTS

| | | | |
|---|---|---|---|
| 976,564 | 11/1910 | Goodson | 128/133 |
| 4,343,299 | 8/1982 | Oxendine | 128/134 X |
| 4,430,990 | 2/1984 | Whitehead | 128/134 X |

FOREIGN PATENT DOCUMENTS

| | | | |
|---|---|---|---|
| 1714 | 3/1820 | France | 128/99 |

*Primary Examiner*—Dalton L. Truluck
*Attorney, Agent, or Firm*—Herbert L. Gatewood

[57] ABSTRACT

A device is provided for wearing during sexual intercourse including a waist band which can be fastened around a person's waist and leg bands for fastening around that person's thighs, the waist and thigh bands being connected together by nonextensible material providing a portion for gripping by one's partner whereby the partner can control the wearer's hip movements, as desired.

2 Claims, 2 Drawing Figures

SEXUAL AID

BACKGROUND OF THE INVENTION (1) Field of the Invention

This invention relates to a device which enables one partner during sexual intercourse to control the hip movement of the other.

(2) Description of Prior Art

Over the years, there have been developed numerous and various products, i.e., sexual aids, for increasing one's sexuality, or stimulating sexual awareness in another, for simulating sex without a partner, and for promoting greater pleasure between and with one's partner during intercourse.

In more recent years, and with the so-called sexual revolution, men and women have become, and are becoming, ever more open, and with one another, about sex, its pleasure, and what each desires the other to do, and how, during intercourse.

None of the various sexual aids heretofore known, as far as I am aware, provide a means whereby one sexual partner can actually control the hip movement of the other during intercourse. Nevertheless, in some positions in which intercourse is practiced, and at certain times, one partner may desire that the other increase his/her hip movement to provide better, deeper, or more rapid penetration.

SUMMARY OF THE INVENTION

There is provided in accordance with the basic aspects of the invention a device whereby one partner can exercise control over the movement of the hips of the other partner during the act of sexual intercourse which comprises:

a. An elongated strip of predetermined length of nonextensible material having first and second ends free but which are capable of being detachably connected together for forming an endless band about said other partner's waist;

b. First and second strips of lesser predetermined length of nonextensible material each having first and second ends which are capable of being detachably connected together for forming an endless band about the thigh of each leg of said other partner;

c. First and second elongated means of nonextensible material of predetermined length each connected at one end thereof to and extending downwardly from said waistband and connected at their other ends to said first and second thigh bands, respectively, whereby said first and second elongated means can be used by said one partner for gripping for controlling the hip movement of the other partner.

In the more preferred embodiment of the invention, the elongated gripping means are detachably connected at their ends to the waistband and thigh bands so that their length can be adjusted as desired making the device of the invention more universally adapted to various physiques.

BRIEF DESCRIPTION OF THE DRAWING

The invention is described in greater detail hereinafter, reference being made to the drawing, to facilitate understanding of the invention, in which.

DETAILED DESCRIPTION OF THE INVENTION AND THE PREFERRED EMBODIMENTS

Figure 1:
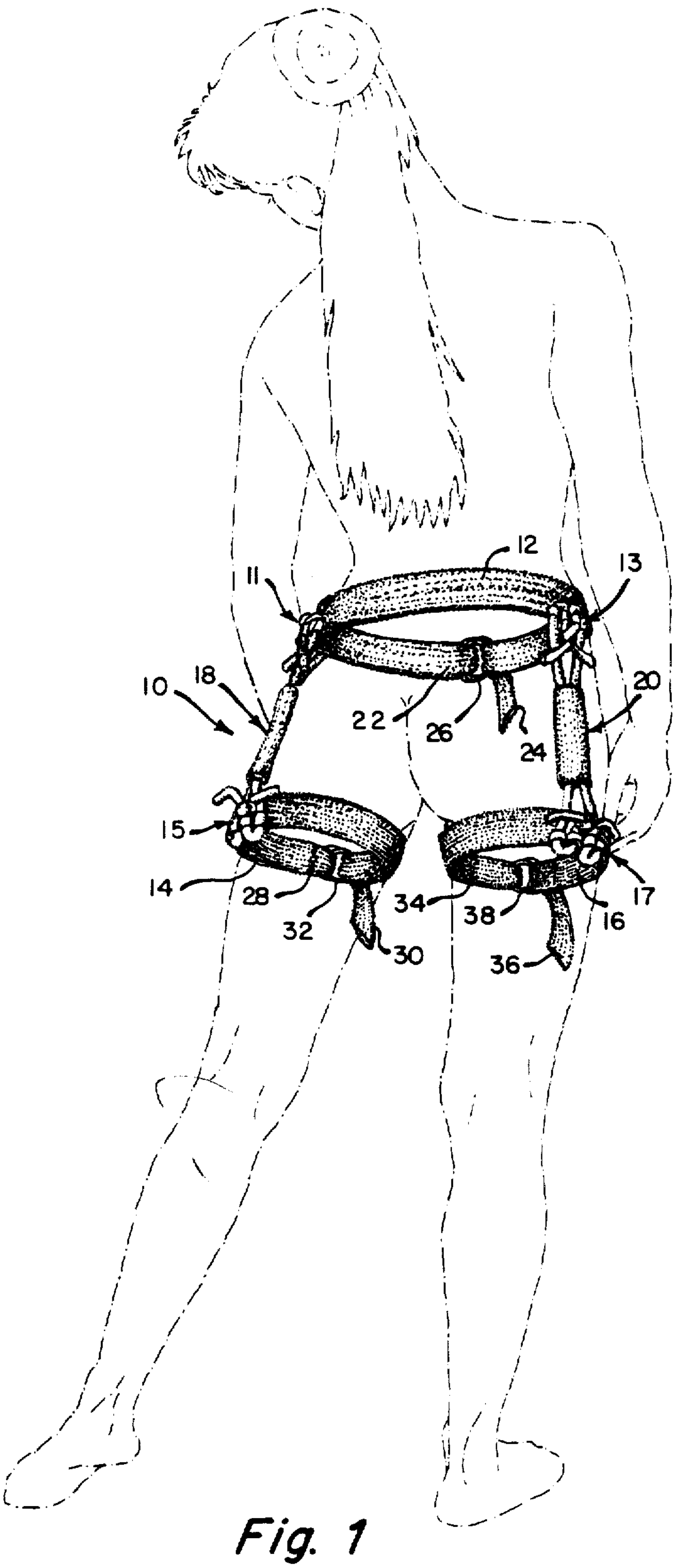
FIG. 1 is a view in perspective showing the device of the invention as worn by a sexual partner during intercourse.

Turning now to the drawing there is shown in FIG. 1 thereof a device 10 in accordance with the invention whereby one partner during the act of sexual intercourse can, if desired, exercise some measure of control over the hip movement of the other partner, i.e., the one wearing device 10. As shown in the drawing, device 10 comprises a waistband or belt 12 connected to first and second leg or thigh bands 14, 16 by first and second means 18, 20, respectively which means, as later more fully disclosed, can be gripped by the one sexual partner during intercourse for controlling the other partner's hip movement.

Waistband 12, as will be seen by reference to FIG. 1 of the drawing, is an elongated strip of material, the length of which is determined by free ends 22, 24. Attached to free end 22 in usual fashion is a conventional D-ring fastening means 26 whereby the two free ends 22, 24 can be fastened together and waistband 12 adjusted to the waist size and tightness desired. Waistband 12 can obviously be of various lengths and widths, the length being dependent somewhat upon the physique of the person who will wear the device. The width should be such that the belt is comfortable without cutting into the flesh. In general, a waistband from about ¾ inch to two inches will be found quite satisfactory.

Leg or thigh bands 14, 16, like waistband 12, are each of a strip of material of predetermined length, thighband 14 having free ends 28, 30, which ends are fastened together, as shown in the drawing, by conventional D-ring fastener 32, connected to free end 28. In similar fashion, the length of thigh band 16 is determined by free ends 34, 36, interconnected together during use by conventional D-ring fastener 38, which, according to usual technique, is fastened to free end 34 by the overlapping thereof around the rings and stitching. These leg bands, like the waistband, can be of various lengths and widths, the length of course being dependent somewhat on the thigh size of the intended user. The width of the thigh band can be the same as that of the waistband, if desired. However, the waist and thigh bands need not be of the same width, provided the requirements set forth above are met.

Although in the preferred embodiment of the invention, as disclosed herein, the free ends of the waist and thigh bands are interconnected together by D-ring fasteners, it will be appreciated that various other fasteners can also be used in the practice of the invention. For example, if desired, the fasteners can be of the so-called Velcro fastening means. Or the fasteners can be buckle-type fasteners. The primary consideration is that the fasteners used allow for some adjustability due to differences in various users' body sizes and providing for more universal application of any particular device. It is desirable also that any fastening means used in the practice of the invention provide ease in the use of the sexual aid device of the invention, i.e., the free ends should be easily interconnected/disconnected together and readily adjustable to particular waist and thigh size, and tightness desired.

Figure 2:
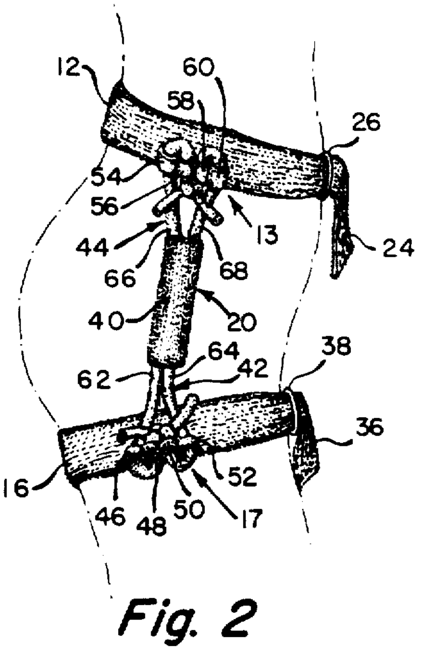
FIG. 2 is a side view of the device shown in FIG. 1 better showing the elongated means for gripping by the other sexual partner.

As will be more readily appreciated by reference to FIG. 2 of the drawing, the gripping means 18, 20 are detachably interconnected to waistband 12 and respective leg bands 14, 16 at waistband loop means 11, 13 and leg band loop means 15, 17. Gripping means 20, as shown in the drawing, has an intermediate gripping portion 40 of predetermined length from the ends of which extend length adjustment means 42, 44, detachably connected, respectively, to thigh band 16 and waistband 12 at the sides thereof at loop means 17 and 13, as hereinafter more fully disclosed.

Loop means 17 and 13 each comprise four individual loops identified respectively by reference numerals 46, 48, 50, and 52; and 54, 56, 58, and 60; however, it will be appreciated that more loops can be provided in each loop means, if desired, dependent somewhat on the length of the waist and leg bands in any particular device of the invention. However, as will be appreciated, in the particular embodiment of the invention disclosed herein, each loop means will necessarily have at least four loops, the reason for which will soon be disclosed, if not already obvious.

The length adjustment means 42, 44 each comprises respectively a pair of connecting ties 62, 64 and 66, 68 of suitable length depending somewhat on the intended user's size. However, it will be appreciated that in the preferred aspect of the invention, the length is such as to allow for adjustability. The free ends of connecting ties 62, 64 are threaded downwardly though outer loops 46, 52, respectively, and then the free ends are threaded upwardly respectively through inner loops 48, 50. The free ends are then tied together in a double over-hand knot, or some other knot providing good secure non-slip fastening, yet ease in untying. In a similar fashion, the free ends of connecting ties 66, 68 are threaded upwardly through outer loops 54, 60 and downwardly through inner loops 56, 58 and then tied together. Gripping means 18 is of the same construction as gripping means 20 and is detachably connected in the same fashion to waistband 12 and leg or thigh band 14. Accordingly, no further description thereof is believed necessary.

It will be appreciated from the construction shown in the drawings and disclosed in this application, that the distance between waistband 12 and the leg bands 14, 16 can be made shorter or longer by pulling more or less of the connecting ties 62, 64 and 66, 68 through the loop means 17, 13. Thus, the device of the invention is somewhat adjustable and can be worn by a relatively wide range of persons having different heights. Nevertheless, it will be appreciated also that in practice it may be desirable to provide the devices of the invention with three or more different standard length connecting ties, to better provide for short, medium, and tall persons. Or the devices of the invention can be provided with connecting ties of maximum length with instructions to cut them off only to some shorter length as desired, allowing for some adjustment and sufficient length for tying off the ends.

The location of loop members 11, 13 on waistband 12 is of some critical importance to obtain the best gripping of the gripping means 18, 20 during use of the device 10. The loop members 11, 13 should be so located on the waistband 12 that when the waistband is fastened around the user's waist, as shown in FIG. 1, the loop members are in opposition to one another on respective sides of the user. The loop means 11, 13 being so located on the waistband 12 will provide that gripping means 18, 20 depend vertically downwardly when the user is standing in erect position, as shown in the drawing. This orientation along the sides of the user will then be maintained on securing leg bands 14, 16. It will be appreciated that although the loop means 15, 17 on the leg bands 14, 16, respectively, should be located during use along a person's sides, the location of these loop means on the respective leg bands is less critical than on waistband 12 as the location of these bands on the user's thighs can be adjusted to accommodate the desired location of the loop means thereon relative to the loop means on the waistband 12. Nevertheless, the location of the loop means on the leg bands should take into consideration that it is most desirable that the leg bands be fastened and unfastened in front, i.e., along the front of the thigh.

Where the loop means are located other than along the sides of waistband 12, as above-disclosed, and as shown in the figures of the drawing, the sexual aid device will be found to perform less satisfactorily, if at all. The location of the loop means more toward the back or front side of the wearer during use, rather than at his/her sides may result in the gripping means being located too far out of reach of the other sexual partner, or at least so that good leverage cannot be obtained to thus control the wearer's hip movements.

As disclosed earlier, the loop means can be provided with a greater number of loops than four, e.g., six, eight, or even more, if desired. The greater the number of loops provided the more readily the device of the invention can be used by a larger group of persons with widely varying waist sizes. Moreover, the greater the number of loops provided in the loop members on any particular waistband, the greater the choice will be in tying off the connecting ties of the gripping means at the best desired orientation for gripping.

The device of the invention can be provided of various materials, the only requirement being that whatever the material used in the manufacture of the device, it should be nonextensible. By this is meant that the material from which the device is manufactured should not be elastic, nor should it be capable of stretching at all to any degree during use. Various such materials are available commercially, e.g., webbing such as is found in military belts and strapping material, leather, and woven fabric materials such as twills. The nonextensible material used can be decorative in and of itself or it can be covered with, or laminated to, a more decorative material, as desired, e.g., a satin or velvet fabric, or lace. A device in accordance with the invention manufactured from commercially available $1\frac{1}{4}$ inch wide strip of Waved Nylon/Polypropylene fabric, style no. 656, Blue Star Mfg., New York, New York, will be found quite satisfactory. The waistband 12 can be manufactured by cutting off a suitable length from a roll of such fabric strip and then turning the longitudinal edges thereof thereover about $\frac{1}{4}$ inch and stitching. The leg bands can be manufactured in similar fashion. One of the free ends of the waistband and each leg band will be threaded in conventional fashion through a D-ring fastener and the running end then stitched down to the standing end. The loop means on the waistband and leg bands can be provided of a suitable length of strip, bunched together to form the desired size loops, and then tacked down at intermittent locations between the loops formed. It will be appreciated that wherever the different components of the device of the invention are joined together by stitching that the stitches must provide secure connections that will not allow separation of the components of the device during use. Rather than stitching with thread, rivets or other suitable fastening means can be used, if desired.

The gripping means can be readily manufactured from a suitable length of strip of material as above-described, folded over and stitched together to provide connecting ties about $\frac{3}{8}$ inch wide. These connecting ties can then be covered and joined at their mid-portions by and to a suitable size strip or portion of fabric, providing for the gripping portion, as identified earlier by reference numeral 40 in FIG. 2 of the drawing. The length of gripping portion 40 will desirably be about the width of the average-size hand.

It will be appreciated that in manufacturing of the waistband and legbands the inside surface thereof, i.e., the side next to the body of the wearer, is desirably flat and smooth without ridges, etc., from stitching and seaming so that the device will feel comfortable while being worn.

In use of the device 10, the device is worn by the sexual partner over whom hip movement control is desired during intercourse, as is shown in phantom in FIG. 1 of the drawing. The free ends of waistband 12 are first joined together and the waistband adjusted to the desired comfortable snugness, making certain that the D-ring fastener on the waistband is located in front and the loop means 11, 13 are located at the sides. Leg bands 14, 16 are then adjusted so that their respective loop means are located along the side of the wearer's thighs, as better shown in FIG. 2 of the drawing. The connecting ties on the gripping means 18, 20 are then adjusted so that any slack is taken up and the gripping of the gripping means will result in positive response and movement of the wearer's hips as desired.

It will be appreciated that the sexual aid device of the invention can be used to advantage by the sexual partners in all the usual positions taken during intercourse. However, its use will be found particularly advantageous where at least one of the sexual partners is in a sitting position. In some cases, it will be desirable that the female partner wear the sexual aid device of the invention. In other cases, it will be found advantageous for the male partner to wear such a device. However, it will also be appreciated that both partners can wear a device according to the invention during sexual intercourse.

It should be understood that the specific embodiments described herein are merely exemplary of the preferred practice of the present invention and that various modifications and changes may be made in the particular embodiments described herein without departure from the spirit and scope of the present invention.

What I claim is:

1. Device whereby one partner can exercise control over the movement of the hips of the other partner during the act of sexual intercourse which comprises:

(a) a waist band of a predetermined length of nonextensible material having first and second free ends, fastening means connected to at least one of said free ends for fastening the ends together to form an endless band around a person's waist, said fastening means providing for adjustability of the waist band size, and loop means each having four individual loops located in opposition to one another on said waist band and so located thereon as to be at the wearer's respective sides when the said device is being worn;

(b) first and second leg bands of a predetermined length of nonextensible material each having first and second free ends, fastening means providing for adjustability connected to at least one of each said first and second free ends for forming an endless band around the wearer's upper thigh, and loop means each having four loops each being provided on each leg band; and (c) first and second gripping means of nonextensible material each having a gripping portion whereby the one partner can grip the device with his hands and a pair of tie connectors extending from each end of the gripping portion for connecting the gripping means to a loop member on the waist band and a loop member on a leg band, said tie connectors being threaded in one direction through the outside loops in the loop means and threaded in the reverse direction through the inner loop and then tied together.

2. Device whereby one partner can exercise control over the movement of the hips of the other partner during the act of sexual intercourse which comprises:

(a) an elongated strip of predetermined length of non-extensible material having first and second ends free, a D-ring fastening means being provided on one of said free ends whereby the two free ends can be detachably connected together for forming an adjustable endless band about said other partner's waist;

(b) first and second strips of lesser predetermined length of nonextensible material each having first and second ends, a D-ring fastening means being provided on one of said first and second ends of each of said strips whereby the said first and second ends in each said strip can be detachably connected together for forming an adjustable endless band about the thigh of each leg of said other partner;

(c) first and second elongated means each comprising an elongated gripping portion of predetermined length and a pair of tie connectors extending from each end of each said gripping portion, and loop means being located on said waist band and each said leg band for the interlacement of said tie connectors and the interconnecting of the waist band to each said leg band, said loop means being located on said waist band at such locations as to be in opposition to one another when the waist band is worn by the said other partner whereby the said elongated means extends downwardly and along each side of said other partner's hip and along each thigh.

* * * * *